(12) United States Patent
Koehler

(10) Patent No.: US 8,246,876 B2
(45) Date of Patent: Aug. 21, 2012

(54) EMBOLIZATION PARTICLES AND METHOD FOR MAKING SAME

(75) Inventor: Cleve Koehler, Center Point, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 457 days.

(21) Appl. No.: 12/193,368

(22) Filed: Aug. 18, 2008

(65) Prior Publication Data
US 2010/0042067 A1  Feb. 18, 2010

(51) Int. Cl.
- B29B 9/06 (2006.01)
- A61L 27/00 (2006.01)
- A61K 9/14 (2006.01)
- A61F 2/02 (2006.01)

(52) U.S. Cl. ........ 264/143; 264/141; 264/142; 264/145; 264/148; 264/151; 427/2.12; 427/2.14; 427/2.31; 424/423; 424/489; 425/106; 425/302.1; 425/315

(58) Field of Classification Search .................. None
See application file for complete search history.

(56) References Cited

U.S. PATENT DOCUMENTS

| | | | |
|---|---|---|---|
| 2,464,746 A * | 3/1949 | Gering | 264/141 |
| 2,887,725 A * | 5/1959 | Vickers et al. | 264/141 |
| 3,837,781 A * | 9/1974 | Lambertus | 425/308 |
| 3,921,874 A * | 11/1975 | Spain | 225/4 |
| 4,025,252 A * | 5/1977 | Hunke | 425/67 |
| 4,486,373 A * | 12/1984 | Kurauchi et al. | 264/142 |
| 5,180,366 A | 1/1993 | Woods | |
| 5,202,352 A | 4/1993 | Okada et al. | |
| 5,258,028 A | 11/1993 | Ersek et al. | |
| 5,573,790 A * | 11/1996 | Wehtje et al. | 425/404 |
| 5,624,685 A | 4/1997 | Takahashi et al. | |
| 5,658,601 A * | 8/1997 | Hoshi | 425/289 |
| 5,716,981 A | 2/1998 | Hunter et al. | |
| 5,823,198 A | 10/1998 | Jones et al. | |
| 5,981,826 A | 11/1999 | Ku et al. | |
| 6,039,905 A * | 3/2000 | Zollitsch et al. | 264/143 |
| 6,171,338 B1 | 1/2001 | Talja et al. | |
| 6,355,275 B1 * | 3/2002 | Klein | 424/490 |
| 6,500,190 B2 | 12/2002 | Greene, Jr. et al. | |
| 6,676,971 B2 * | 1/2004 | Goupil et al. | 424/489 |
| 7,053,134 B2 * | 5/2006 | Baldwin et al. | 522/154 |
| 7,094,369 B2 * | 8/2006 | Buiser et al. | 264/7 |
| 7,131,997 B2 | 11/2006 | Bourne et al. | |
| 7,156,880 B2 | 1/2007 | Evans et al. | |
| 7,588,825 B2 * | 9/2009 | Bell et al. | 428/402 |

(Continued)

FOREIGN PATENT DOCUMENTS

WO  WO2008049241  * 5/2008

*Primary Examiner* — Jeffrey Wollschlager
(74) *Attorney, Agent, or Firm* — Brinks Hofer Gilson & Lione

(57) ABSTRACT

In at least one embodiment of the present invention, a method for making embolization particles for occluding fluid flow through a body vessel is provided. The method comprises positioning an elongated body of biocompatible material relative to a cutting device. The elongated body is defined by extrusion of a body cross-section along a longitudinal axis. The elongated body is cut with a cutting device at a plurality of locations along the longitudinal axis to form the embolization particles such that each of the embolization particles has a particle cross-section that corresponds to the body cross-section.

10 Claims, 3 Drawing Sheets

U.S. PATENT DOCUMENTS

| | | | |
|---|---|---|---|
| 7,785,512 B1* | 8/2010 | Pathak | 264/211 |
| 2003/0134032 A1 | 7/2003 | Chaouk et al. | |
| 2003/0204246 A1* | 10/2003 | Chu et al. | 623/1.23 |
| 2005/0060017 A1 | 3/2005 | Fischell et al. | |
| 2005/0095428 A1* | 5/2005 | Dicarlo et al. | 428/402 |
| 2006/0136071 A1 | 6/2006 | Maspero et al. | |
| 2006/0177513 A1* | 8/2006 | Martin et al. | 424/489 |
| 2007/0067045 A1 | 3/2007 | Phan et al. | |
| 2009/0269390 A1* | 10/2009 | Luo et al. | 424/426 |
| 2010/0311638 A1* | 12/2010 | Tiege | 514/1.1 |

* cited by examiner

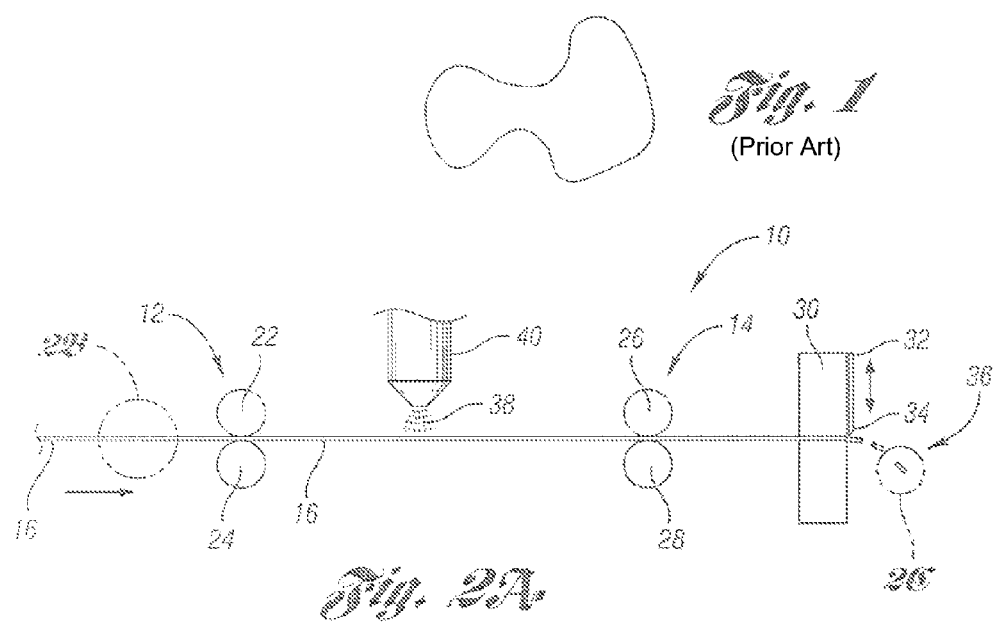
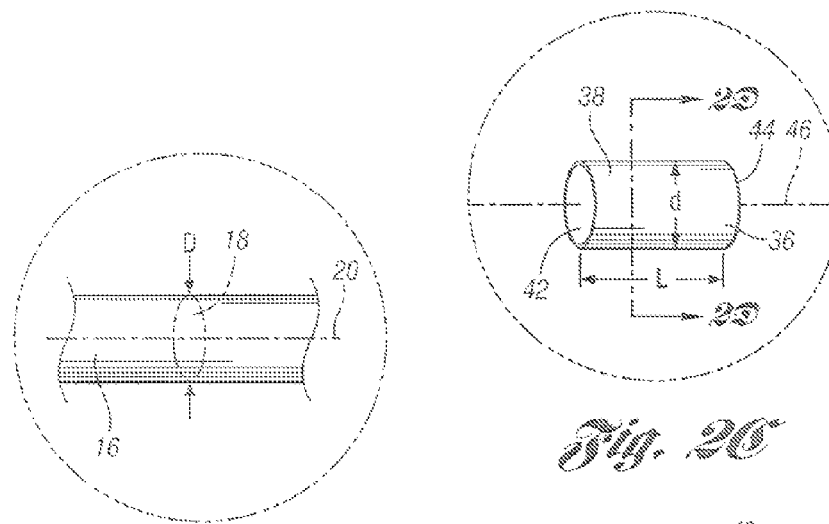

EMBOLIZATION PARTICLES AND METHOD FOR MAKING SAME

BACKGROUND OF THE INVENTION

1. Field of the Invention

The present invention relates to embolization particles and a method for making embolization particles.

2. Background of the Invention

Embolization particles are generally particles in an injectable composition that may be introduced or injected into the body via a catheter or other suitable device to form occlusive masses in a selected body region. For example, the composition may be introduced into the human body to block blood flow to portions of malfunctioning human organs, e.g., the kidney, spleen or liver, or to block blood flow into malfunctioning regions of a blood vessel such as arterio-denous malformations (ADM) and aneurysms. The compositions may also be used to occlude vessels providing blood to both malignant and to benign tumors.

There are a variety of materials and devices which have been used for embolization. These include platinum and stainless steel micro-coils, and polyvinyl alcohol particles, including polyvinyl alcohol sponges, to name just a few. In the case of particle or sponge embolization materials, the effectiveness of the particles to form occlusion masses and the precision of placement of these masses depends on the particles tendencies to be dispensed and/or congregated. More specifically, the particles are preferably produced and selected to complement the liquid medium used to carry the particles in the body without plugging or tending to plug the device used to introduce the material into the body. At the same time, however, the particles preferably congregate and pack themselves together once they are delivered to a desired location within the body. Particle shape and consistency is important in predictably balancing these two preferred, yet contradicting functions.

Currently, methods for making embolization particles typically involve forming a block of material, such as for example, a polyvinyl alcohol foam block and bulk shredding the block to form the particles. However, due to the bulk processing of these particles, the respective shapes may vary considerably despite efforts to sort the particles according to their size. FIG. 1 illustrates an example of an embolization particle having a varying shape randomly formed by bulk shredding.

In practice, when an interventionalist selects the embolization particles, she does so typically based on particle size. Her experience regarding the particle size suggests to her how the particles are likely to behave in a given clinic scenario. However, because the shapes of these particles may vary considerably, their performance may also correspondingly vary.

BRIEF SUMMARY OF THE INVENTION

In satisfying the above need and overcoming the above and other drawbacks and limitations of the known technology, the present invention provides a method for making embolization particles for occluding fluid flow through a body vessel. The method comprises positioning an elongated body of biocompatible material relative to a cutting device. The elongated body is defined by extrusion of a body cross-section along a longitudinal axis. The elongated body is cut with the cutting device at a plurality of locations along the longitudinal axis to form the embolization particles such that each of the embolization particles has a particle cross-section that corresponds to the body cross-section.

In one aspect, the elongated body and the cutting device are moved relatively towards each other and the particle cross-section substantially matches the body cross-section.

In at least one embodiment of the present invention, an embolization kit for occluding fluid flow through a body vessel is provided. The kit comprises a plurality of embolization particles formed of biocompatible material. Each of the embolization particles have two opposing surfaces and a longitudinal axis extending between the two opposing surfaces. Extrusion of a cross-section between the opposing surfaces along the longitudinal axis defines each of the embolization particles. A microcatheter is configured to be positioned within the body vessel and to deploy the embolization particles.

In at least one other embodiment of the present invention, a method for occluding fluid flow through a body vessel is provided. The method comprises positioning a distal end of a microcatheter within the body vessel. Embolization particles as discussed in the foregoing paragraph are deployed from the distal end of the microcatheter into the body vessel.

Further aspects, features, and advantages of the invention will become apparent from consideration of the following description and the appended claims when taken in connection with the accompanying drawings.

BRIEF DESCRIPTION OF THE DRAWINGS

FIG. 1 is a side view of a prior art embolization particle;

FIG. 2a is a side view of an apparatus for making embolization particles in accordance with an embodiment of the present invention;

FIG. 2b is an enlarged side view of an elongated member depicted in FIG. 2a;

FIG. 2c is an enlarged prospective view of an embolization particle depicted in FIG. 2a;

FIG. 2d is a sectional view of the embolization particle depicted in FIG. 2c;

FIG. 3c is a partial sectional view of a microcatheter depicted in FIG. 3a;

DETAILED DESCRIPTION OF THE INVENTION

Figures 3A, 3B:
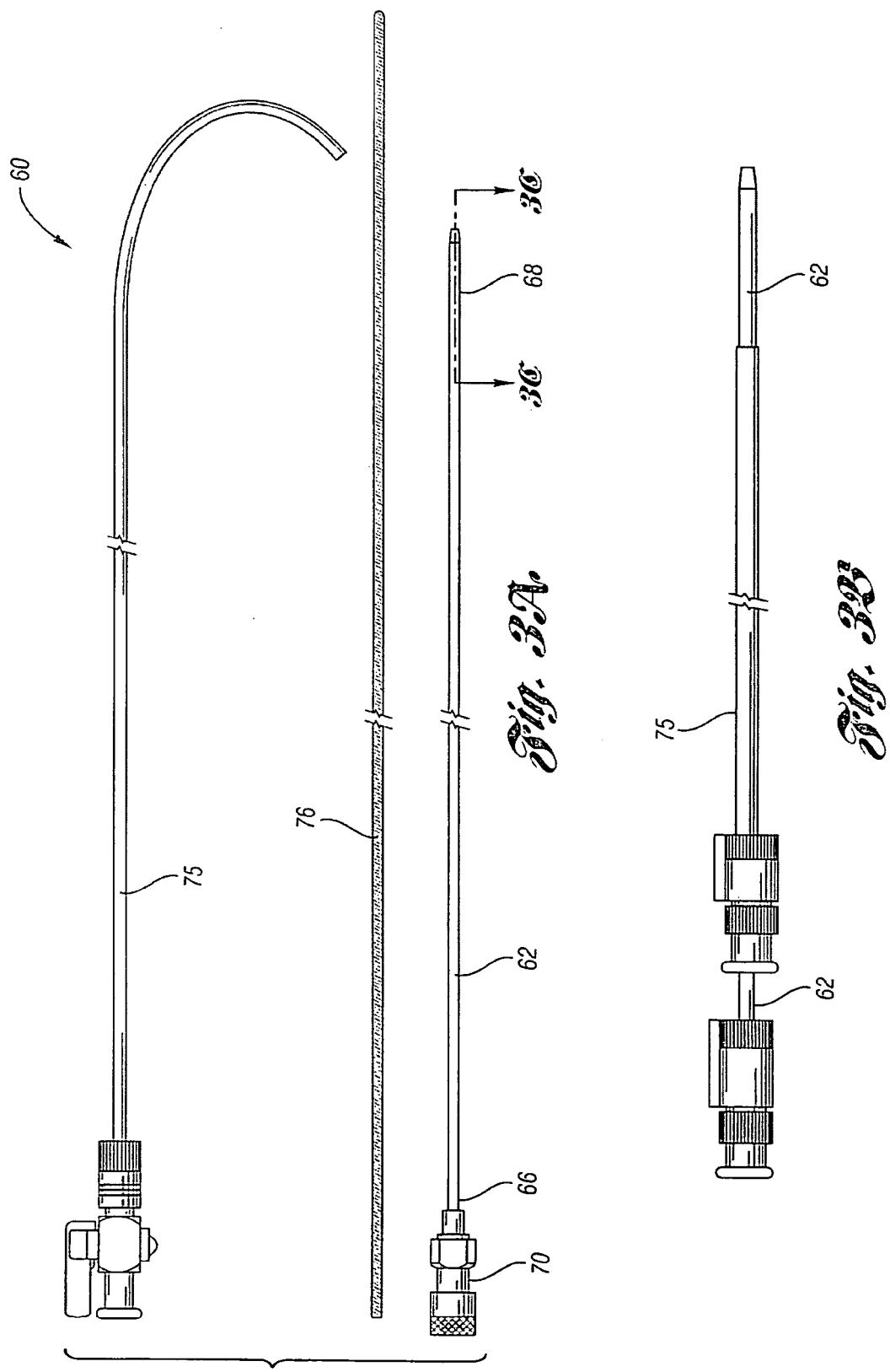
FIG. 3a is an exploded view of an embolization kit in accordance with an embodiment of the present invention.
FIG. 3b is a side view of an embolization kit in accordance with an embodiment of the present invention.

Detailed embodiments of the present invention are disclosed herein. It is understood however, that the disclosed embodiments are merely exemplary of the invention and may be embodied in various and alternative forms. The figures are not necessarily to scale; some figures may be configured to show the details of a particular component. Therefore, specific structural and functional details disclosed herein are not to be interpreted as limiting but merely as a representative basis for the claims and teaching one skilled in the art to practice the present invention.

The present invention seeks to overcome some of the problems associated with varying shapes resulting from bulk production of embolization particles as discussed in the foregoing section. Preferably, the present invention provides a method for making embolization particles that have more predictable and consistent shapes.

"Embolization particle" is a generic term for a particle used to artificially block blood flow. Embolization of a vessel to an organ or in an organ may be used for a number of reasons. Vessel embolization may be used, for instance, for 1) controlling a bleeding caused by trauma, 2) prevention of profuse blood loss during an operation requiring dissection of blood vessels, 3) obliteration of a portion of or of a whole organ having a tumor, or 4) blocking of blood flow into normal blood vessel structures such as AVM's and aneurysms.

The present invention employs a more uniform cutting or slicing approach to making embolization particles, which preferably allows for improved control over the shape and consistency of the particles. More specifically, the embolization particles are formed by cutting through or slicing an elongated body, e.g., a strand of material, crosswise relative to its elongated form. The elongated body has an extruded shape with substantially uniform or consistent cross-sections formed throughout. By slicing the elongated body substantially transverse to its longitudinal axis, the embolization particles will have cross-sections that correspond to cross-sections of the elongated body, providing particles with more consistent shapes.

Referring to FIGS. 2a-2d, an apparatus for making embolization particles in accordance with an embodiment of the present invention is provided. The apparatus 10 includes tensioning members 12 and 14 which are spaced apart. The tensioning members 12 and 14 may be configured as a plurality of tensioning rollers 22, 24, 26 and 28 which cooperate to tension and advance an elongated body or strand 16. Alternatively, the tensioning members 12 and 14 may be guiding plates (not shown) which cooperate to tension and guide the strand 16. Other suitable means for tensioning and positioning the strand 16 may also be used.

The strand 16 is formed from a biocompatible material. The biocompatible material may be a non-biodegradable material, such as for example, glass (E-glass, S-glass or otherwise) or a non-biodegradable polymer, e.g., PTFE. Alternatively, the biocompatible material may be a biodegradable polymer, such as for example, polylactic acid (PLA), poly (glycolic acid) (PGA), copolymers of the PLA and PGA, or polycaprolactone (PCL). These synthetic biopolymers exhibit good mechanical properties. Moreover, the degradation products, such as glycolic acid for PGA, are also non-toxic and easily metabolized by the body.

The biocompatible material may include various types of additives. In one embodiment, the biocompatible material contains a radiopacifier. The radiopacifier is detectable within the body of a patient by fluoroscopic visualization and/or X-ray and thus, allows an interventionalist to monitor its location when positioned within a patient's body.

In another embodiment, the biocompatible material contains a medicant additive. The medicant may be homogenously dispersed throughout the biocompatible material or alternatively, be positioned in discrete areas or regions within or about the biocompatible material, e.g., forming either an outer, intermediate or inner layer with the biocompatible material for example via a co-extrusion process or the alike. The medicant may include but is not limited to a compound or compounds to promote blood clotting, an antiangiogenic which inhibits the growth of new blood vessels, or a cytotoxic drug used to stop the proliferation of cancer cells. For instance, the biocompatible material may be a synthetic biopolymer which has trapped chemotherapeutic agents within. Inside the body of the patient, the polymer degrades and the chemotherapeutic agents can diffuse into the immediately adjacent tissue. The rate of degradation of the biopolymer may be tailored to control the diffusion of the chemotherapeutic agent (or other medicant) for a specific medical application and accordingly, may be rapid, slow or anywhere therebetween.

The strand 16 may be formed by extrusion or pultrusion of the biocompatible material, such as for example, through a forming die or mold (not shown). For instance, the mold may have an orifice formed therethrough. The biocompatible material, e.g. polymer, may be extruded via an extruder (not shown) through the orifice to define the strand 16 having substantially uniform cross-sections 18 formed along a longitudinal axis 20 of the strand 16. Note—"substantially uniform" is hereinafter understood to mean "uniform to within typical manufacturing tolerances." In one example, the cross-section 18 of the strand 16 is substantially circular being formed, for example, through a circular orifice. Preferably, the cross-section 18 of the strand 16 has a diameter (D) in the range of about 100 to 400 µm.

Moreover, the tensioning members 12 and 14 may cooperate with the extruder and mold to further tension the strand 16, which may be in a heated and softened state from the extrusion process, thinning out the strand 16 and further defining the cross-section 18. The strand may be subsequently cooled or become cooled during the tensioning process, e.g., natural or forced convection, to dimensionally stabilize the strand 16. Other suitable means and shapes for forming the strand 16 known to those skilled in the art may also be used.

In at least one embodiment, the strand 16 is coated with a medicant 38 (notably, in other embodiments the strand 16 may be without a medicant 38 coating). The medicant coating 38 may be sprayed on the strand 16 via a coating spray device 40. The thickness of the coating 38 may be relatively thin, such as for example, on the order of several angstroms, however, thicker coatings 38 may be used without departing from the present invention. Preferably, the strand 16 is coated during tensioning between the two tensioning members 12 and 14 and the medicant coating 38 is allowed to sufficient dry and/or coalesce and/or cure prior to being cut by a cutting device 32, as will be discussed in greater detail below, to prevent pre-deployment agglomeration of the embolization particles 36. Alternatively, the strand 16 may be coated before or after tensioning. Other suitable means for coating the strand 16 with a medicant 38 may also be used, e.g., dip coating the strand 16 into or through medicant 38 or as previously mentioned the strand 16 may include a co-extruded layer of the medicant 38.

In one embodiment, the tensioning members 12 and 14 cooperate to move the strand 16 towards a cutting device 32 which may include a guide member 30. Alternatively, the guide member 30 may be distinct from the cutting device 32 but positioned proximate to or immediately adjacent to the cutting device 32. In one example, the cutting device 32 has at least one cutting or shearing element 34. The guide member 30 may have an opening formed therethrough for guiding the stand 16 towards the cutting element 34. Other suitable arrangements for guiding the strand 16 toward the cutting element 34 and/or cutting device 32 may also be used.

The guide member 30 positions the strand 16 such that the cutting element 34 preferably cuts or shears through the strand 16 across its longitudinal axis 20 at a plurality of locations to form a plurality of embolization particles 36. The resulting embolization particles 36 each have a longitudinal axis 46 and cross-section 48 corresponding to the longitudinal axis 20 and the cross-section 18 of the strand 16. In one example, the cross-sections 48 of the embolization particles 36 are substantially circular having a diameter (d) in the range of about 100-400 μm. In another example, the diameter (d) of the embolization particles 36 are substantially equal to or match the diameter (D) of the strand 16. Notably, when the strand 16 is coated with the medicant 38, the diameter (D) of the strand 16 includes the thickness of the coating 38 and accordingly, the diameter (d) of the particle 36 includes the thickness of the coating 38.

In the example illustrated in FIG. 2a, the cutting element 34 slices through the stand 16 at a plurality of locations along the longitudinal axis 20 via up-down stroking motions. The strokes may be timed at predetermined or regular intervals with the strand 16 being feed to the cutting device 32 at a constant rate to produce embolization particles 36 with substantially uniform lengths (L). In one example, the strand 16 is cut multiple times to produce embolization particles 36 having opposed cut surfaces 42 and 44, which are substantially planar and/or parallel, and the lengths of the embolization particles 36 are preferably within the range of about 300-500 μm. In another example, the feed rate of the strand 16 and/or the stroking intervals of the cutting element 34 are varied to produce embolization particles 36 having a distribution of different lengths (L). Other suitable stroking or cutting motions of the cutting element 34 or other suitable cutting devices 32, e.g., lasers, may be used to cut the strand 16.

In one embodiment, the guide member 30 includes a means for advancing the strand 16 towards the cutting element 34. For example, the guide member 30 may include internal rollers (not shown) which rotationally engage and advance the strand 16. The internal rollers may cooperate with the tensioning members 12 and 14 to both tension and feed the strand 16 to the cutting element 34. Other suitable means for feeding the strand 16 to the cutting element 34 and/or cutting device 32 may also be used.

Figure 3C:
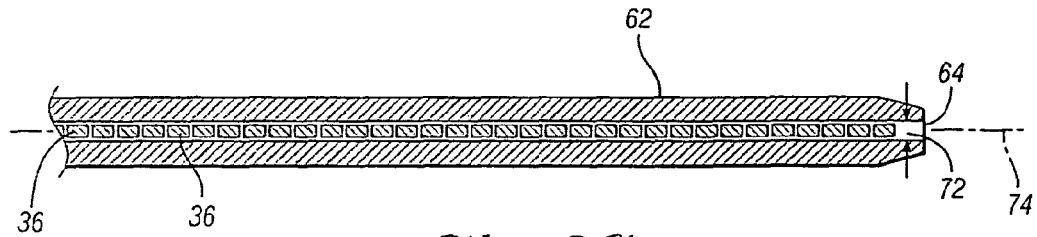

Referring to FIGS. 3a-3c, a body vessel embolization kit which implements the embolization particles in accordance with at least one embodiment of the present invention is provided. As shown, the kit 60 includes a microcatheter 62 defining a catheter lumen 64 and is preferably made of a soft, flexible material such as silicone or any other suitable material. Generally, the microcatheter 62 has a proximal end 66, and a distal end 68, and a plastic adapter or hub 70. In one example, the hub 70 receives the embolization particles 36 to be advanced therethrough, such as for example, in a mixture or slurry with a fluid, e.g., saline solution, as will be discussed in further detail below. In another example, the embolization particles 36 may be pre-packaged within the lumen 64 of the microcatheter 62 and advanced therethrough by advancing a fluid, e.g., saline solution, contrast media, a mixture thereof or the alike, through the hub 70 as will also be discussed in further detail below.

The kit 60 may further include a guide catheter 75 and a guide wire 76 which provides the guide catheter 75 a path during insertion of the guide catheter 75 within a body vessel. The size of the guide wire 76 is based on the inside diameter of the guide catheter 75.

In one embodiment, the guide catheter 75 is a polytetrafluoroethylene (PTFE) guide catheter or sheath for percutaneously introducing the microcatheter 62 into a body vessel. Of course, any suitable material may be used without falling beyond the scope or spirit of the present invention. The guide catheter 75 may have a size of about 4-8 french and allows the microcatheter 62 to be inserted therethrough to a desired location in the body vessel. The guide catheter 75 receives the microcatheter 62 and provides stability of the microcatheter 62 at a desired location within the body vessel. For example, the guide catheter 75 may stay stationary within a common visceral artery, e.g., a common hepatic artery, adding stability to the microcatheter 62 as the microcatheter 62 is advanced through the guide catheter 75 to a point of occlusion in a connecting artery, e.g., the left or right hepatic artery.

When the distal end 68 of the microcatheter 62 is at a point of occlusion in the body vessel, the embolization particles 36 may be loaded at the proximal end 66 via the hub 70 of the microcatheter 62. In one example, saline solution is mixed with the embolization particles to form a slurry which is injected into the hub 70 of the microcatheter 62 and advanced through the lumen 64. Alternatively and as illustrated in FIG. 3c, the embolization particles 36 may be pre-loaded within the lumen 64 of the microcatheter 62. In this example, the lumen 64 has a cross-section 72 that corresponds to the cross-sections 48 of the particles 36 so as to position the particles 36 such that their longitudinal axes 46 are aligned with each other and with a central longitudinal axis 74 of the lumen 64. Saline solution or other suitable transferring fluid is introduced at the proximal end 66 of the microcatheter 62 to advance the embolization particles 36 to the distal end 68 of a lumen 64. It is believed that providing the embolization particles 36 with such a consistent orientation facilitates or insures deeper penetration of the particles 36 into the body vessel, such as for example, into a tumor vascular bed. Alternatively, a push wire (not shown) may be used to mechanically advance or push the embolization particles 36 through the microcatheter 62. The size of the push wire depends on the diameter of the microcatheter 62.

It is to be understood that the body vessel embolization kit described above is merely one example of a kit that may be used to deploy the embolization particles into the body vessel. Of course, other kits, assemblies, and systems may be used to deploy any embodiment of the embolization particles without falling beyond the scope or spirit of the present invention, such as for example, a microcatheter having two lumens; one lumen for advancing the embolization particles, and the second lumen for being advanced along the guide wire to a desired point of occlusion.

Notably, the present invention as discussed in the foregoing paragraphs provides at least two means for delivering a medicant to a targeted body vessel site. Specifically, the medicant may be delivered either as incorporated into the biocompatible material of the embolization particles 36 or as a coating on the embolization particles 35. Preferably, the local delivery of the medicant includes minimizing the side affects to the healthy tissues which may otherwise be an issue if delivered systematically to treat certain illnesses or conditions.

Figure 4:
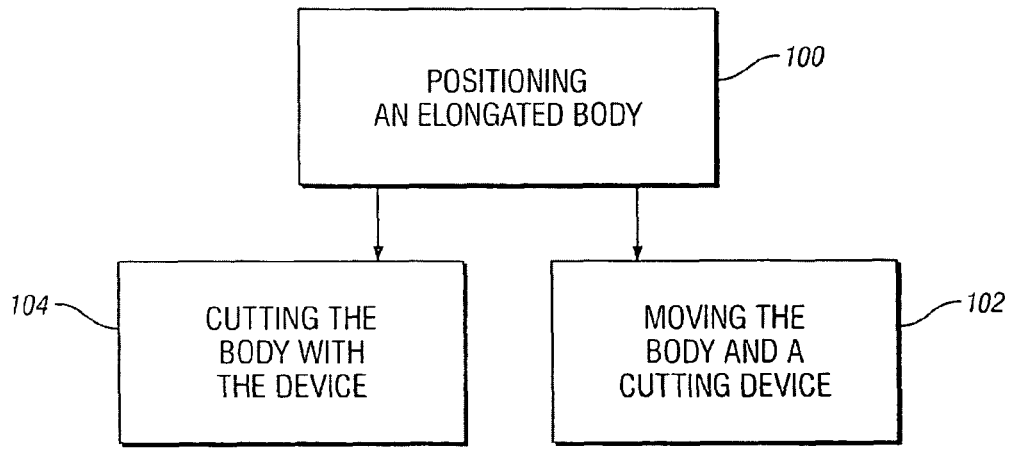
FIG. 4 is a flow chart of one example of a method for making embolization particles in accordance with the present invention.

Referring to FIG. 4, a method for making embolization particles for occluding fluid flow through a body vessel is provided. The method comprises positioning an elongated body at 100 of biocompatible material relative to a cutting device. The elongated body is defined by extrusion of a body cross-section along a longitudinal axis. The step of positioning includes moving the elongated body and a cutting device at 102 relative towards each other. The elongated body is cut with the cutting device at 104 at a plurality of locations along the longitudinal axis to form the embolization particles such that each of the embolization particles has a particle cross-section that corresponds to the body cross-section.

Figure 5:
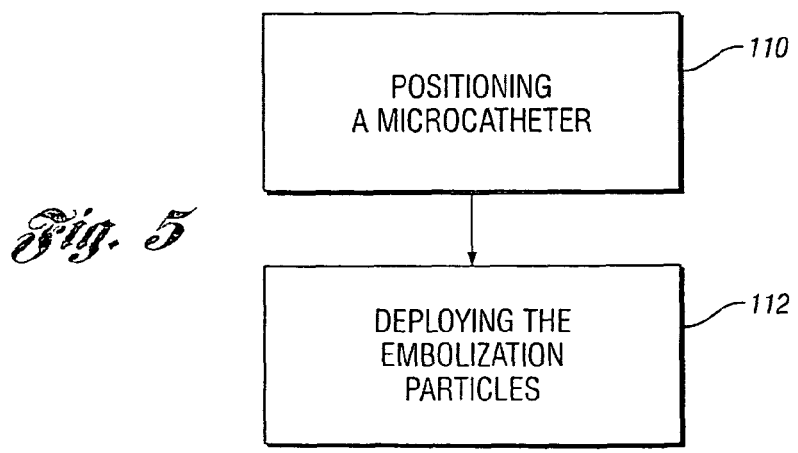
FIG. 5 is a flow chart of one example of a method for occluding fluid flow through a body vessel in accordance with the present invention.

Referring to FIG. 5, a method for occluding fluid flow through a body vessel in accordance with one embodiment of the present invention is provided. The method includes positioning a distal end of a microcatheter at 110 within a body vessel. A plurality of embolization particles formed of biocompatible material are deployed at 112 from the distal end of the microcatheter into the body vessel. Each of the embolization particles have two opposing surfaces and a longitudinal axis extending between the two opposing surfaces and are defined by extrusion of a cross-section between the opposing surfaces along the longitudinal axis.

In one example, the microcatheter has a lumen in fluid communication with the distal end. The lumen has a diameter corresponding to the cross-sections of the embolization particles. The step of deploying the embolization particles includes advancing the embolization particles through the lumen to the distal end of the microcatheter such that the longitudinal axes of the embolization particles are aligned with each other and with the central longitudinal axis of the lumen.

As a person skilled in the art will readily appreciate, the above description is meant as an illustration of the implementation of the principles of this invention. This description is not intended to limit the scope or application of this invention in that the invention is susceptible to modification, variation, and change, without departing from the spirit of this invention as defined in the following claims.

I claim:

1. A method for making embolization particles for occluding fluid flow through a body vessel, the method comprising:
    moving an elongated body of biocompatible material relatively towards a guide member and a cutting device, the elongated body defined by extrusion of a body cross-section along a longitudinal axis, the guide member having an opening formed therethrough for guiding the elongated body toward the cutting device;
    tensioning the elongated body between at least two tensioning members, the tensioning members being longitudinally spaced apart along the elongated body;
    coating the elongated body with a medicant;
    feeding the elongated body through the opening of the guide member toward the cutting device, the guide member being disposed downstream of the tensioning members; and
    cutting the elongated body with the cutting device at a plurality of locations along the longitudinal axis to form the embolization particles such that each of the embolization particles has a particle cross-section that substantially matches the body cross-section.

2. The method according to claim 1 wherein the body cross-section is substantially circular.

3. The method according to claim 2 wherein the body cross-section has a diameter in the range of about 100 to 400 µm.

4. The method according to claim 1 wherein the plurality of locations along the longitudinal axis are spaced apart in the range of about 300 to 500 µm.

5. The method according to claim 1 wherein the step of cutting includes cutting the elongated body transverse to the longitudinal axis at the plurality of locations.

6. The method according to claim 1 wherein the biocompatible material includes a biodegradable polymer.

7. The method according to claim 1 wherein the cutting device includes one of a shearing element and a laser for cutting the elongated body.

8. The method according to claim 1 wherein the step of coating the elongated body with a medicant is performed during the step of tensioning the elongated body.

9. The method according to claim 1 further comprising coating the elongated body with a medicant by one of spray coating and dip coating the medicant onto the elongated body.

10. The method according to claim 1 wherein the biocompatible material contains an additive comprising at least one of a medicant and a radiopacifier.

* * * * *